United States Patent
Sexton et al.

(10) Patent No.: US 10,870,115 B2
(45) Date of Patent: Dec. 22, 2020

(54) EVACUATED BLOOD COLLECTION TUBES CONTAINING PROTEASE INHIBITORS FOR THE ASSESSMENT OF CONTACT SYSTEM ACTIVATION

(71) Applicant: Dyax Corp., Lexington, MA (US)

(72) Inventors: Daniel J. Sexton, Melrose, MA (US); Ryan Faucette, Melrose, MA (US)

(73) Assignee: Dyax Corp., Lexington, MA (US)

( * ) Notice: Subject to any disclaimer, the term of this patent is extended or adjusted under 35 U.S.C. 154(b) by 116 days.

(21) Appl. No.: 15/752,228

(22) PCT Filed: Aug. 12, 2016

(86) PCT No.: PCT/US2016/046681
§ 371 (c)(1),
(2) Date: Feb. 12, 2018

(87) PCT Pub. No.: WO2017/027771
PCT Pub. Date: Feb. 16, 2017

(65) Prior Publication Data
US 2019/0022641 A1   Jan. 24, 2019

Related U.S. Application Data

(60) Provisional application No. 62/214,308, filed on Sep. 4, 2015, provisional application No. 62/204,644, filed on Aug. 13, 2015.

(51) Int. Cl.
*A61B 5/154* (2006.01)
*C07K 16/40* (2006.01)
(Continued)

(52) U.S. Cl.
CPC ........ *B01L 3/5082* (2013.01); *A61B 5/15003* (2013.01); *A61B 5/154* (2013.01);
(Continued)

(58) Field of Classification Search
CPC .......... B01L 3/5082; B01L 2300/0832; B01L 2200/16; G01N 33/96; G01N 33/573; G01N 33/564; G01N 2333/96433; C07K 16/40
See application file for complete search history.

(56) References Cited

U.S. PATENT DOCUMENTS

2005/0124965 A1   6/2005   Haywood
2008/0286818 A1*  11/2008  Datwyler ............. G01N 33/573
                                                435/7.93
(Continued)

FOREIGN PATENT DOCUMENTS

CN   101467038 A   6/2009
CN   102353569 A   2/2012
(Continued)

OTHER PUBLICATIONS

Cugno et al., Parallel reduction of plasma levels of high and low molecular weight kininogen in patients with cirrhosis. Thromb Haemost. Nov. 1999;82(5):1428-32.
(Continued)

*Primary Examiner* — Jennifer Wecker
*Assistant Examiner* — Michael Paul Shimek
(74) *Attorney, Agent, or Firm* — Wolf, Greenfield & Sacks, P.C.

(57) ABSTRACT

Disclosed herein are evacuated blood collection tubes comprising protease inhibitor cocktails in liquid form and uses thereof for assessing features associated with the contact system in a subject, including the endogenous level of contact system activation, the endogenous level of a drug that targets a component of contact system during treatment, and/or the immunogenicity of such a drug.

20 Claims, 5 Drawing Sheets
Specification includes a Sequence Listing.

(51) Int. Cl.
*G01N 33/564* (2006.01)
*G01N 33/573* (2006.01)
*G01N 33/96* (2006.01)
*B01L 3/00* (2006.01)
*A61B 5/15* (2006.01)

(52) U.S. Cl.
CPC ........ *A61B 5/150755* (2013.01); *C07K 16/40* (2013.01); *G01N 33/564* (2013.01); *G01N 33/573* (2013.01); *G01N 33/96* (2013.01); *B01L 2200/16* (2013.01); *B01L 2300/0832* (2013.01); *G01N 2333/96433* (2013.01)

(56) References Cited

U.S. PATENT DOCUMENTS

| | | | | |
|---|---|---|---|---|
| 2012/0288504 A1* | 11/2012 | Smith | ................ | G01N 33/6863 424/135.1 |
| 2013/0209985 A1* | 8/2013 | Hoke | ................ | A61B 5/15003 435/2 |
| 2014/0030754 A1* | 1/2014 | Craft | ................... | A61B 5/1438 435/29 |

FOREIGN PATENT DOCUMENTS

| | | |
|---|---|---|
| CN | 203203992 U | 9/2013 |
| CN | 103814046 A | 5/2014 |
| CN | 104244902 A | 12/2014 |
| JP | 2005-525126 A | 8/2005 |
| JP | 2013-505438 A | 2/2013 |
| JP | 2014-500482 A | 1/2014 |
| WO | WO 98/19161 | 5/1998 |
| WO | WO 03/097237 A2 | 11/2003 |
| WO | WO 2007/140963 A1 | 12/2007 |
| WO | WO 2013/116702 A1 | 8/2013 |
| WO | WO 2014/121041 A1 | 8/2014 |
| WO | WO 2015/061183 A1 | 4/2015 |

OTHER PUBLICATIONS

Galbusera et al., A novel interpretation of the role of von Willebrand factor in thrombotic microangiopathies based on platelet adhesion studies at high shear rate flow. Am J Kidney Dis. Oct. 2000;36(4):695-702.

Konings et al., Ongoing contact activation in patients with hereditary angioedema. PLoS One. Aug. 27, 2013;8(8):e74043. doi: 10.1371/journal.pone.0074043.

Motellón et al., Parathyroid hormone-related protein, parathyroid hormone, and vitamin D in hypercalcemia of malignancy. Clin Chim Acta. Jan. 5, 2000;290(2):189-97.

* cited by examiner

EVACUATED BLOOD COLLECTION TUBES CONTAINING PROTEASE INHIBITORS FOR THE ASSESSMENT OF CONTACT SYSTEM ACTIVATION

CROSS REFERENCE TO RELATED APPLICATIONS

This application is a national stage filing under 35 U.S.C. § 371 of international application number PCT/US2016/046681, filed Aug. 12, 2016, which claims the benefit of the filing date of U.S. Provisional Application No. 62/204,644 filed Aug. 13, 2015 and U.S. Provisional Application No. 62/214,308, filed Sep. 4, 2015. The entire contents of each of these referenced applications are incorporated by reference herein.

BACKGROUND OF THE INVENTION

Accurate measurement of the in vivo level of contact system activation using patient plasma is challenging due to the propensity for ex vivo activation during blood collection. Blood from patients with certain diseases associated with the contact system, e.g., hereditary angioedema, is especially prone to ex vivo contact system activation since it is deficient in C1 inhibitor, the natural inhibitor of the pathway. Consequently, measurements of pathway specific biomarkers (e.g., 2-chain high molecular weight kininogen) may overestimate the degree of contact system activation that is present within the patient, unless the blood is carefully collected and processed.

SUMMARY OF THE INVENTION

The present disclosure is based, at least in part, on the development of non-glass evacuated blood collection tubes containing protease inhibitor mixtures (cocktails) in liquid formulation, which prevents ex vivo activation of the contact system during blood collection. As such, the evacuated blood collection tubes described herein allow for accurate measurement of the endogenous level of contact system activation of patients, particularly those who are deficient in a natural inhibitor (e.g., C1 inhibitor) of this pathway.

Accordingly, one aspect of the present disclosure features an evacuated blood collection tube, comprising a liquid formulation that comprises a mixture of protease inhibitors, which may be substantially free of protease inhibitors that are unstable in an aqueous solution. The tube may be a non-glass tube. In some embodiments, the tube is plastic. In some embodiments, the evacuated blood collection tube contains 0.5 ml of any of the liquid formulations described here, which can be diluted by 10-fold in use.

In some embodiments, the mixture of protease inhibitors in the evacuated blood collection tube described herein comprises at least one serine protease inhibitor (e.g., a plasma kallikrein inhibitor) and at least one cysteine protease inhibitor. In one example, the mixture of protease inhibitors comprises EPI-KAL2, which may be biotinylated, and leupeptin. The amount of EPI-KAL2 may range from 5 to 15 µM in the liquid formulation containing such. Alternatively or in addition, the amount of leupeptin may range from 200 to 300 µM in the liquid formulation.

In some embodiments, the mixture of protease inhibitors described herein may comprise at least two serine protease inhibitors, at least one of which is a trypsin inhibitor, for example, soybean trypsin inhibitor. In some examples, the mixture of protease inhibitors comprises benzamidine, soybean trypsin inhibitor, leupeptin, and AEBSF. In some examples, the liquid formulation in the evacuated blood collection tube may comprise 80-120 mM benzamidine, 1-3 mg/ml soybean trypsin inhibitor, 200-300 µM leupeptin, and/or 10-30 mM AEBSF.

The liquid formulation in any of the evacuated blood collection tubes described herein may further comprise polybrene and EDTA. In some embodiments, any of the liquid formulations described herein may have a pH of 4-6 (e.g., 4.5).

In another aspect, the present disclosure provides a method for assessing the endogenous level of contact system activation in a subject. The method comprises: (i) collecting blood from a subject to any of the evacuated blood collection tubes described herein; (ii) processing the blood to produce a plasma sample; and (iii) measuring the level of contact system activation in the plasma sample. In some embodiments, the measuring step (step (iii)) can be carried out by measuring the level of one or more biomarkers indicative of contact system activation. Such biomarkers may comprise prekallikrein, active plasma kallikrein (pKal), α2M-pKal complex, active factor XII, active factor XI, high molecular weight kininogen (HMWK), and/or a bradykinin metabolite. In one example, the one or more biomarkers comprise cleaved HMWK and/or intact HMWK.

In yet another aspect, the present disclosure provides a method for assessing the level of a drug targeting contact system in a subject. The method comprises: (i) collecting blood from a subject to an evacuated blood collection tube as described herein, wherein the subject is administered with a drug that targets a component of the contact system; (ii) processing the blood to produce a plasma sample; and (iii) measuring the level of the drug in the plasma sample.

Further, the present disclosure provides a method for assessing immunogenicity of a drug targeting contact system, the method comprising: (i) collecting blood from a subject to an evacuated blood collection tube as described herein, wherein the subject is administered a drug that targets a component of the contact system; (ii) processing the blood to produce a plasma sample; and (iii) measuring the level of antibodies that bind to the drug in the plasma sample. Such a method may further comprise, prior to step (iii), isolating antibodies that bind the drug from the plasma sample. In some examples, the anti-drug antibodies (ADAs) can be isolated by a solid phase extraction and acid dissociation (SPEAD) assay.

In any of the methods described herein, the subject can be a human patient, who, in some instances, may be treated with a drug targeting a component (e.g., plasma kallikrein) of the contact system, for example, a drug (e.g., an antibody) specifically targeting plasma kallikrein (e.g., the active form of plasma kallikrein). In some examples, the blood is derived from a human patient having a disease associated with the contact system, e.g., hereditary angioedema (HAE) or idiopathic angioedema. In some instances, the human patient has HAE with normal C1-inhibitor (C1-INH).

In any of the methods described herein, the evacuated blood collection tube may not be the first tube filled with blood from the subject. Alternatively or in addition, the process step [step (ii)] can be performed within one hour after the blood collecting step [step (i)].

The details of one or more embodiments of the invention are set forth in the description below. Other features or advantages of the present invention will be apparent from the following drawings and detailed description of several embodiments, and also from the appending claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

DETAILED DESCRIPTION OF THE INVENTION

Figure 1:
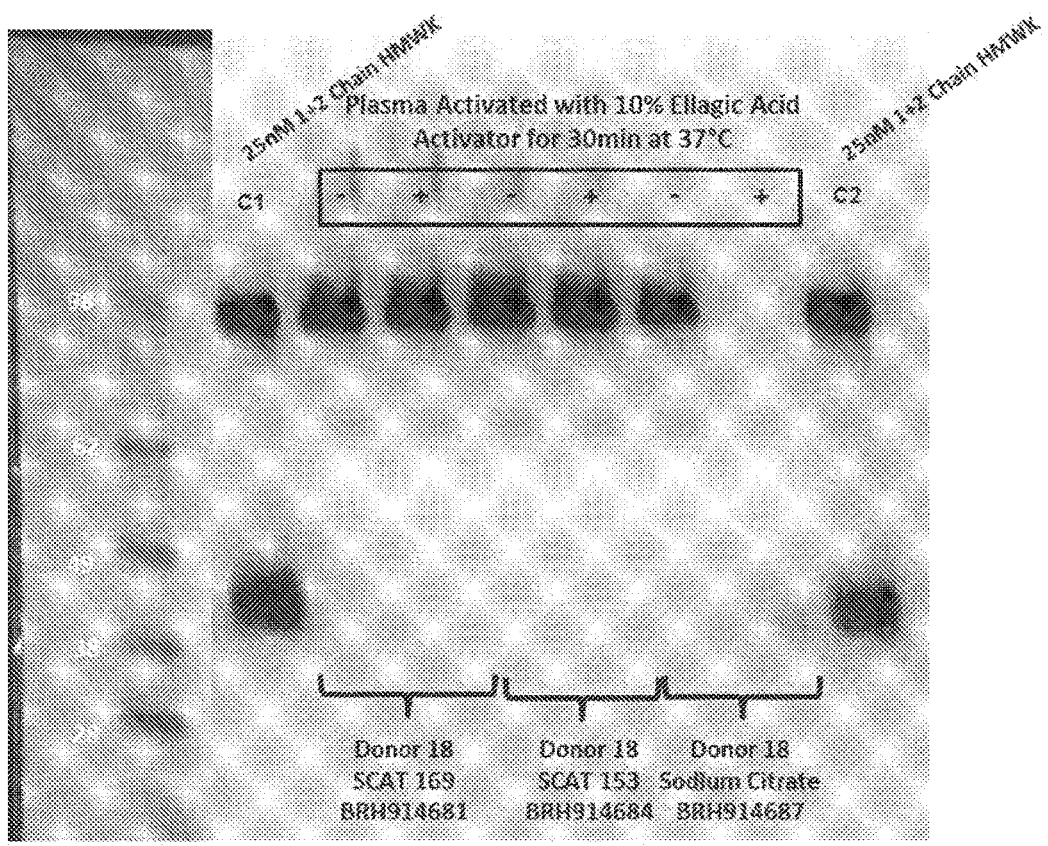
FIG. 1 is a photo showing that the SCAT169 and SCAT153 tubes prevented contact activation as measured in a 2-Chain Western blot assay. When 10% ellagic acid is added to the plasma, the contact system is activated leading to the conversion of 1-chain HMWK to 2-chain HMWK (see the Sodium citrate plasma). In contrast, the SCAT169 and SCAT153 plasma contains the same amount of 1-chain HMWK pre- and post-addition of the ellagic acid.

The present disclosure is based, at least in part, on the development of evacuated blood collection tubes comprising protease inhibitor cocktails that prevent contact system activation. In order to accurately assess the endogenous level of contact system activation in a patient or a healthy volunteer, it is critical that blood is carefully collected and processed. One or more of the following precautions may be taken to ensure accurate assessment of features associated with the contact system as described herein:
  (i) The evacuated blood collection tubes described herein are preferred not to be the first tube filled with blood, which can show elevated contact system activation due to the local trauma following vessel puncture by the needle;
  (ii) The blood may not come into contact with glass (use plastic tubes or catheters);
  (iii) The blood may be processed to plasma within a short period of time (e.g., ~1 hour) after collection; and/or
  (iv) The use of protease inhibitors in the collection tube may stabilize the plasma against ex vivo contact activation which masks accurate determination of endogenous patient status.

The advantages of the evacuated blood collection tubes described herein include, at least: (1) the use of evacuated non-glass (e.g., plastic) tubes for standardized and simplified blood collection; (2) the use of a liquid formulation comprising the protease inhibitor cocktails to minimize hydrolysis; (3) optional omission of protease inhibitors that are unstable in aqueous solutions (e.g., PPACK II, also known as H-D-Phe-Phe-Arg-chloromethyl ketone); and (4) inclusion, in some embodiments, of a plasma kallikrein inhibitor such as EPI-KAL2 (may be biotinylated), which offers the ability for the tubes to contain a reagent that permits detection of activated plasma kallikrein using an immunoassay. See, e.g., WO95/21601, the relevant disclosures thereof are incorporated by reference herein.

An unexpected observation from this study was that the use of the protease inhibitor cocktail in liquid form prevented or reduced hemolyzation. When blood was collected into evacuated tubes containing a lyophilized preparation of the protease inhibitors, it was largely hemolyzed, which may interfere with certain analyte measurements. However, when blood is collected into an evacuated tube containing a solution of the same protease inhibitor mixture, it was not hemolyzed.

Consequently, measurements directed at assessing the degree of contact system activation in plasma samples processed from blood samples collected in the evacuated tubes described herein provide more accurate assessment levels from patients with different diseases. Obtaining an accurate estimate of contact activation can allow for identification of diseases or subsets of patients with different diseases that are potentially mediated by this pathway and therefore amenable to treatment with an inhibitor of the contact system.

Further, the use of the evacuated blood collection tubes described herein can facilitate the accurate determination of drug levels and/or immunogenicity assessment for a therapeutic molecule directed against activated forms of proteins in the contact system (e.g., plasma kallikrein, FXIIa, and 2-chain kininogen). The tubes may offer a similar advantage for therapeutic molecules targeted to activated proteins downstream of the contact system activation that do not require calcium for the generation of the activated target (e.g., FXIa, and FIXa). The advantage of these tubes primarily applies to biologic therapeutic molecules since the PK and immunogenicity assays used are typically immunoassays that recognize the binding site (e.g., the idiotype, in the case of a therapeutic antibody). If the therapeutic target is activated ex vivo, it can bind the biologic present in the plasma and thereby mask detection in the PK and immunogenicity immunoassays. The protease inhibitors in the tubes can prevent the target activation. The use of the liquid formulation prevents hemolysis, which can interfere in certain laboratory assays.

Evacuated Blood Collection Tubes Containing Protease Inhibitor Cocktails in Liquid Formulation Evacuated blood collection tubes are commonly used in medical practices for collecting blood samples for various uses. The tubes described herein may be non-glass tubes comprising a liquid formulation that comprises a mixture of protease inhibitors (a protease inhibitor cocktail). In some embodiments, the protease inhibitor cocktail may comprise at least one serine protease inhibitor and at least one cysteine protease inhibitor. At least one serine protease inhibitor can be a plasma kallikrein inhibitor. Such protease inhibitor cocktails may comprise multiple (e.g., 2, 3, 4, or 5) serine protease inhibitors, at least one of which can be a trypsin or human plasmin inhibitor. Preferably, the protease inhibitor cocktails described herein are substantially free of a protease inhibitor that is unstable in an aqueous solution, i.e., the activity of the protease inhibitor that is unstable in an aqueous solution is insubstantial as relative to the total inhibitory activity of the protease cocktail. In some instances, the amount of the protease inhibitor that is unstable in an aqueous solution may be less than 5% (w/w) of the total protease inhibitors in the cocktail, e.g., less than 2%, less than 1%, or less than 0.5%. In some instances, the protease inhibitor cocktail is completely free of a protease inhibitor that is unstable in an aqueous solution (e.g., an aqueous solution having a pH of 4-6). One example of protease inhibitor that is not stable in an aqueous solution is PPACK II, also known as H-D-Phe-Phe-Arg-chloromethyl ketone.

Table 1 below lists exemplary serine protease inhibitors, cysteine protease inhibitors, and trypsin protease inhibitors, which can be used for making the protease inhibitor cocktails described herein.

| Categories | Exemplary Inhibitors |
|---|---|
| Serine Protease Inhibitors | * Benzamidine<br>* 4-(2-Aminoethyl) benzenesulfonyl fluoride hydrochloride (AEBSF);<br>* * Chymostatin;<br>* Nalpha-Tosyl-Lys Chloromethyl Ketone (TLCK);<br>* Tos-Phe-CH2Cl; N-p-Tosyl-L-phenylalanine chloromethyl ketone (TPCK)<br>* 1-({(6R,7S)-3-[(acetyloxy)methyl{-7-methoxy-5,5-dioxido-8-oxo-5-thia-1-azabicyclo[4.2.0]oct-2-en-2-yl}carbonyl)-L-proline<br>* Patamostat mesylate;<br>*Gabexate mesylate;<br>* Msaapvck (Meosuc-aapv-cmk; MeOSuc-Ala-Ala-Pro-Val-CMK)<br>* Nafamostat mesylate;<br>* Rosmarinic acid;<br>* Purpurogallin;<br>* 2-(4-((1-Acetimidoyl-3-pyrrolidinyl)oxy)phenyl)-3-(7-amidino-2-naphthyl)propanoic acid hydrocloride pentahydrate<br>* 4-(4-Bromophenylsulfonylcarbamoyl)benzoyl-L-valyl-L-proline-1(RS)-(1-trifluoroacetyl-2-methylprolyl)amide<br>*L-658758; CHEMBL446371; L 658758<br>* Sivelestat;<br>* Patamostat;<br>* Cholesterol sulfate;<br>* Elastase Inhibitor III;<br>* Gabexate;<br>* 4',6-Diamidino-2-phenylindole;<br>* 4-aminobenzamidine;<br>* 3,4-dichloroisocoumarin;<br>* Bivalirudin Trifluoroacetate<br>* Pradaxa;<br>* HIRUDIN;<br>* Ximelagatran;<br>* Lepirudin; Refludan; Hbw 023<br>* Bivalirudin;<br>* Letaxaban;<br>* Eribaxaban;<br>* Dabigatran etexilate mesylate;<br>* Apixaban;<br>* Tanexaban;<br>* Rivaroxaban; Xarelto; 366789-02-8<br>* Plasma kallikrein inhibitors such as EPL-KAL2, DX-88, DX-2930, etc.<br>The following examples are trypsin and/or human plasmin inhibitors:<br>* Soybean trypsin inhibitor<br>* 4-(2-aminoethyl)benzenesulfonylfluoride<br>* 4-aminobenzamidine<br>* alpha 1-Antitrypsin<br>* Aprotinin<br>* Camostat<br>* Eco protein (*E coli*)<br>* inter-alpha-inhibitor<br>* Nafamostat<br>* NCO 650<br>* Ovomucin<br>* Somatomedin B<br>* Trypsin Inhibitor (Bowman-Birk Soybean)<br>* Trypsin Inhibitor (Kunitz Soybean)<br>* Urinastatin |
| Cysteine Protease Inhibitor | * Geldanamycin; 30562-34-6; AKOS022185390<br>* Calpastatin;<br>* L-Proline,N-[[2S,3S)-3-[(propylamino)carbonyl]-2-oxiranyl]carbonyl]-L-isoleucyl-;<br>* Proteasome Inhibitor I;<br>* (L-3-trans-(Propylcarbamyl)oxirane-2-carbonyl)-L-isoleucyl-L-proline; |

| Categories | Exemplary Inhibitors |
|---|---|
| | * Calpain Inhibitor III;<br>* [L-3-trans-(Propylcarbamoyl)oxirane-2-carbonyl]-L-isoleucyl-L-proline;<br>* Omuralide;<br>* (S)-MG132;<br>* Lactacystin;<br>* Z-Phe-ala-diazomethane;<br>* Leupeptin;<br>* 4-Hydroxynonenal;<br>* trans-Epoxysuccinyl-L-leucylamido(4-guanidino)butane;<br>* Loxistatin;<br>* Clasto-lactacystinbeta-lactone;<br>* L-Proline,<br>* Z-FA-FMK;<br>* N-acetylleucyl-leucyl-methioninal;<br>* nitroaspirin;<br>* Allnal;<br>* Aloxistatin;<br>* ethyl 3-({4-methyl-1-[(3-methylbutyl)amino]-1-oxopentan-2-yl}carbamoyl)oxirane-2-carboxylate;<br>* (+/−)4-HYDROXYNON-2-ENAL; |

In some examples, the protease inhibitor cocktail for use in making the evacuated blood collection tubes comprises at least one serine protease inhibitor (e.g., 1, 2, or 3), which may include at least one trypsin/plasmin inhibitor (e.g., 1, 2, or 3), and at least one cysteine protease inhibitor (e.g., 1, 2, or 3). Such a protease inhibitor cocktail may comprise three serine protease inhibitors (e.g., benzamidine, AEBSF, and a trypsin/plasmin inhibitor such as soybean trypsin inhibition) and one cysteine protease inhibitor (e.g., leupeptin).

In other examples, the protease inhibitor cocktail may comprise at least one serine protease inhibitor (e.g., a plasma kallikrein inhibitor) and at least one cysteine protease inhibitor (e.g., leupeptin). The plasma kalikrein inhibitor may be EPI-KAL2 (Met His Ser Phe Cys Ala Phe Lys Ala Asp Asp Gly Pro Cys Arg Ala Ala His Pro Arg Trp Phe Phe Asn Ile Phe Thr Arg Gln Cys Glu Glu Phe Ser Tyr Gly Gly Cys Gly Gly Asn Gln Asn Arg Phe Glu Ser Leu Glu Glu Cys Lys Lys Met Cys Thr Arg Asp; SEQ ID NO: 1), which is a specific plasma kallikrein, recombinant protease inhibitor that offers the ability for the tubes to contain a reagent that permits detection of activated plasma kallikrein using, e.g., immunoassays.

Any of the protease inhibitor cocktails may be dissolved in a suitable solution to form a liquid formulation. The suitable solution may be an acid-citrate-dextrose solution, which may comprise trisodium citrate, citric acid, and dextrose. The solution may have a pH value of about 4-6, 4-5, 4.5-5.0, or 4.2-4.7, e.g., 4.5. In some embodiments, the solution has a pH value of about 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0. In some embodiments, the solution has a pH value of about 4.5. The liquid formulation may further comprise a cationic polymer such as hexadimethrine bromide molecule (Polybrene®), which can reduce contact system activation by interaction with negatively charged surfaces and a chelating agent (e.g., EDTA), which can inhibit metalloproteases.

The concentration of each of the protease inhibitors in the cocktail may be 5× or 10× higher than the final concentration of such an inhibitor for use in inhibiting the corresponding protease, depending upon the dilution fold in practice. The final concentration of a specific commercially protease inhibitor was known in the art and can be obtained from manufacturer's protocol. In some examples, the concentration of EPI-KAL2 may range from 5-15 μM (e.g., 5-10, 7 to 12 μM, or 10-15 μM). In some embodiments, the concentration of EPI-KAL2 is about 5, 6, 7, 8, 9, 10, 11, 12, 13, 14, or about 15 μM. In some examples, the concentration of leupeptin may range from 200-300 μM (e.g., 200-250, 240-270, or 250-300 μM). In some embodiments, the concentration of leupeptin is about 200, 210, 220, 230, 240, 250, 260, 270, 280, 290, or about 300 μM. In some examples, the concentration of soybean trypsin inhibitor may range from 1-3 mg/ml (e.g., 1-2 or 2-3 mg/ml). In some embodiments, the concentration of soybean trypsin inhibitor is about 1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or about 3.0 mg/mL. In some examples, the concentration of benzamidine can range from 80-120 mM (e.g., 80-100 or 100-120 mM). In some embodiments, the concentration of benzamidine is about 80, 85, 90, 95, 100, 105, 110, 115, or about 120 mM. In some examples, the concentration of AEBSF may range from 10-30 mM (e.g., 10-20 or 20-30 mM). In some embodiments, the concentration of AEBSF is about 10, 11, 12, 13, 14, 15, 16, 17, 18, 19, 20, 21, 22, 23, 24, 25, 26, 27, 28, 29, or about 30 mM.

When a peptide-based protease inhibitor (e.g., EPI-KAL2) is used, it may be biotinylated following conventional methodology. For example, the peptide inhibitor may be biotinylated as follows. Briefly, the peptide inhibitor can be dissolved in a suitable solution, such as phosphate-buffered saline (PBS). Freshly prepared Sulfo-NHS-LC-Biotin can be added to the peptide inhibitor solution and incubated on ice for a suitable period of time. Excess non-reacted and hydrolyzed biotin can be removed using a spin-desalting column. The labeling of the peptide inhibitor can be confirmed by ELISA and the protein concentration can be determined, for example, by the Bradford assay.

Any of the liquid formulations described herein can be prepared by routine methods, e.g., dissolving the proper components into a suitable solution, and placed in evacuated blood collection tubes, which preferably is non-glass. The tubes may be stored at −20° C. and may be thawed on ice or at refrigerated temperatures (e.g., about 4° C.), such as in a refrigerator within a suitable period of time prior to use.

Utilities of Evacuated Blood Collection Tubes Comprising Protease Inhibitor Cocktails in Liquid Form Any of the evacuated blood collection tubes described herein can be used to collect blood samples from subjects for use in analyzing endogenous features associated with the contact system, including, but not limited to, the level of contact system activation, the serum level of a drug that targets a component of the contact system, and/or the immunogenicity of such a drug. To reduce ex vivo activation of the contact system (e.g., by local trauma following vessel puncture by the needle), the evacuated blood collection tubes described herein may not be the first tube filled with blood when drawing blood from a subject. For example, the initial blood from the subject may be collected in a first tube, which may be discarded, and then the evacuated blood collection tubes are used to collect the subsequent blood samples, which can be used for analysis. The first tube may be a regular blood collection tube used in routine practice.

After blood collection, the blood samples may be processed to produce plasma samples within a suitable period of time (e.g., not exceeding an hour). The plasma samples can be subject to further analysis to assess features associated with the contact system of the subject from whom the initial blood sample is obtained.

The blood samples may be collected from a subject in need of the analysis as described herein. In some instances, the subject is a human patient, who may have, be suspected of having, or be at risk for a disease associated with the contact system. For example, the human patient may have a prior occurrence of HAE or may be at risk for HAE. The human patient may have type I or type II HAE, who either is deficient in C1-INH or produces an atypical C1-INH. Alternatively, the human patient may have type III HAE, which is not connected with C1-INH deficiency. In other examples, the human patient may have a prior occurrence of idiopathic angioedema or may be at risk for idiopathic angioedema. Such a human patient may have been treated previously or be in the course of treatment with a drug that targets a component of the contact system (e.g., pKal or FXIIa or high molecular weight kininogen).

i. Assessing Endogenous Level of Contact System Activation

In one aspect, the plasma samples noted herein can be analyzed to assess the endogenous level of contact system activation of a subject, which maybe a human patient having, suspected of having, or at risk for a disease associated with the contact system (e.g., HAE or idiopathic angioedema). Such a human patient may be on a treatment of the disease, for example, a treatment involving a pKal inhibitor (e.g., an anti-pKal antibody). In other instances, such a human patient may be free of such a treatment. Alternatively, the human subject may be a healthy subject having no such diseases.

The level of contact system activation of the plasma sample can be determined by measuring one or more biomarkers indicative of contact system activation.

Plasma kallikrein (pKal) is the primary bradykinin-generating enzyme in the circulation. The activation of pKal can occur via the contact system or via Factor XIIa, both of which have been linked to disease pathology associated with hereditary angioedema (HAE). Plasma kallikrein circulates as an inactive zymogen called prekallikrein that is mostly bound to its substrate high molecular weight kininogen (HMWK). In response to a stimulus, prekallikrein is cleaved to form active plasma kallikrein. This activation of kallikrein can be mediated, e.g., by Factor XIIa after activation of FXII to FXIIa, or by an effector of the contact cascade. Approximately 75-90% of circulating prekallikrein is bound to HMWK through a non-active site interaction with domain 6 of HMWK that will hydrolyze additional molecules of HMWK to generate cleaved HMWK and bradykinin. Active plasma kallikrein cleaves HMWK at two sites, resulting in the release of Bradykinin, a key mediator of pain, inflammation, edema and angiogenesis. The other cleavage product, cleaved kininogen, comprises to amino acid chains held together by a disulfide bond. Cugno et al., Blood (1997) 89:3213-3218.

Exemplary biomarkers that can be used to assess the level of contact system activation in a patient blood sample (thus determining whether the patient has an elevated level and/or activity of the contact system, e.g., an elevated level or activity of pKal), are provided in Table 2 below:

TABLE 2

Contact System Biomarkers

| Biomarker | Assay | Basal Level in HAE patient relative to normal | Δ indicating or during acute edema attack |
|---|---|---|---|
| Prekallikrein | ELISA or enzyme activity assay | Unchanged (~500 nM) or slightly decreased | Decreased further |
| Active pKal | ELISA or enzyme activity | Unchanged or slightly increased | Increased |
| α2M-pKal complex | ELISA | Elevated, if recent attack | Increased |
| C1INH-pKal complex | ELISA | Elevated, if recent attack | Increased |
| FXIIa | ELISA or enzyme activity | Unchanged or slightly increased | Increased |
| FXIa | ELISA or enzyme activity | Unchanged or slightly increased | Increased |
| Intact HMWK | ELISA | Unchanged or slightly decreased | Decreased |
| Cleaved HMWK | ELISA | Unchanged or slightly increased | Increased |
| Bradykinin metabolite | ELISA or LC-MS | Unchanged or slightly increased | Increased |

One or more of the biomarkers indicative of contact system activation may be analyzed using convention methods. One particularly suitable type of assay for detecting, either qualitatively, semi-quantitatively, or quantitatively, is immunoassays. An immunoassay is any assay in which a target molecule (e.g., a biomarker molecule associated with contact system activation) is detected and/or quantified by using a binding agent as described herein that specifically binds the target molecule. The binding agent may be an antibody, which can be a full-length antibody or an antigen-binding fragment thereof. The immunoassay may be a competitive or a non-competitive immunoassay, and may be a homogeneous or a heterogeneous immunoassay. For example, the immunoassay for detecting a contact system biomarker may be an enzyme immunoassay (EIA), radio-immunoassay (RIA), fluoroimmunoassay (FIA), chemiluminescent immunoassay (CLIA), counting immunoassay (CIA), immunoenzymometric assay (IEMA), enzyme-linked immunosorbent assay (ELISA), a lateral flow immunoassay, a sandwich immunoassay, an immuno-PCR assay, a proximity ligation assay, a western blot assay, or an immunoprecipitation assay. Additional suitable immunoassays for detecting a biomarker provided herein will be apparent to those of skill in the art. It will be apparent to those of skill in the art that this disclosure is not limited to immunoassays, however, and that detection assays that are not based on an antibody or an antigen binding antibody fragment, such as mass spectrometry, are also useful for the detection and/or quantification of contact system biomarkers as provided herein.

The type of detection assay used for the detection and/or quantification of a contact system biomarker such as those provided herein will depend on the particular situation in which the assay is to be used (e.g., clinical or research applications), and on the kind and number of biomarkers to be detected, and on the kind and number of patient samples to be run in parallel, to name a few parameters. For example, elevated levels of cleaved kininogen (2-chain kininogen) can be detected in plasma samples collected from HAE patients or healthy subjects during an acute HAE episode using a Western blot assay. While Western blot assays allow for the simultaneous analysis of contact system biomarkers in a plurality of samples, they are limited in the number of biomarkers that can be assessed in parallel. Accordingly, in some embodiments, where a plurality of contact system biomarkers provided herein is analyzed in a single sample, or in multiple samples, assays suitable for such multiplex analysis are preferred. Examples for such assays include, without limitation, peptide microarrays and lab-on-a-chip assays, which have been designed to offer a high throughput, multiplex-ready alternative to less scalable immunoassays such as Western blots.

In some examples, a plasma sample can be placed in a multi-well microplate in the presence or absence of a pKal inhibitor and/or a contact system activator. The mixture can be incubated on ice in the presence of a labeled peptide substrate of pKal for a suitable period of time (e.g., 2 minutes), and corn trypsin inhibitor (CTI) can be added to the mixture to stop the activation reaction. The mixture can be diluted if necessary and the proteolytic activity can be determined by measuring the level of a fluorescent peptide substrate. The results obtained form such an assay can be relied on to determine the endogenous level of contact system activation of the subject from whom the plasma sample is obtained. They also can be relied on to determine the inhibitory activity of the pKal inhibitor, if used.

ii. Assessing Endogenous Levels of Drugs Targeting the Contact System

Another aspect of the present disclosure pertains to the use of the evacuated blood collection tubes described herein for the determination of the levels of a drug targeting a component of the contact system. Drug levels are required to evaluate pharmacokinetic parameters. For example, if the contact system is activated ex vivo in plasma samples collected for the determination of amount of a plasma kallikrein inhibitor (e.g., DX-2930) in plasma, then the excess activated plasma kallikrein could bind the drug and thereby mask its detection in an assay. Any of the evacuated blood collection tubes described herein can be used to more accurately estimate drug levels, for example in a sample collected from a subject.

To practice this method, plasma samples derived from a subject (e.g., a human patient) treated with a drug that targets a component of the contact system (e.g., pKal) may be prepared from blood samples collected in the evacuated blood collection tubes described herein following the methods also described herein. The level of the drug in the plasms sample can be measured following routine practice. In some instances, the drug level can be measured by an immunoassay, e.g., those described herein.

iii. Assessing Immunogenicity of Drugs Targeting the Contact System

Another aspect of the present disclosure pertains to the use of the evacuated blood collection tubes for the determination of the immunogenicity of a biologic inhibitor against a component of the contact system (e.g., pKal). For example, it is common practice to develop immunogenicity assays that are able to measure antibodies against the drug ("ADAs") in the presence of excess drug in the plasma of the circulation. This requirement for an immunogenicity assay that can measure ADAs is certainly the case for therapeutic monoclonal antibodies, which can have multiple week half-lives and high drug levels in the circulation. To overcome the interference due to excess drug in the sample, techniques are performed to separate anti-drug antibodies from the drug. Such anti-drug antibodies may be isolated by solid phase extraction and acid dissociation (SPEAD), which involves incubation of a biotinylated form of the drug with the plasma sample for an extended period of time (usually overnight) followed by isolation of the biotinylated drug that may be bound to anti-drug antibodies using a streptavidin coated plate. The plate is then treated with acid to release the anti-drug antibodies. The released antibodies may be coated directly on another assay plate for detection. In the absence of protease inhibitors in the collection tubes, the contact system can become activated ex vivo, leading to the production of active plasma kallikrein. After the acid releasing and re-coating steps noted above, both active pKal and anti-drug antibodies would bind to the surface of the plate. The anti-drug antibody is typically detected using a labeled drug, which could also bind to active pKal, if present, resulting in a false positive signal in the ADA assay.

The use of the evacuated blood collection tubes that comprise the protease inhibitor cocktails described herein can prevent this false positive signal.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1: Preparation of Protease Inhibitor Cocktails that Prevent Contact System Activation Protease inhibitor cocktails that prevented contact system activation were developed. Evacuated plastic tubes were used for standardized and simplified blood collection.

The following two protease inhibitor cocktails were utilized in a liquid formulation to prevent hydrolysis:

1) 10× Protease Inhibitor Cocktail A: SCAT169

Evacuated 5 mL total volume plastic tubes containing (0.5 ml): 100 mM benzamidine, 400 µg/mL polybrene, 2 mg/mL soybean trypsin inhibitor, 20 mM EDTA, 263 µM leupeptin, and 20 mM AEBSF (4-(2-Aminoethyl) benzenesulfonyl fluoride hydrochloride) dissolved in acid-citrate-dextrose (100 mM trisodium citrate, 67 mM citric acid, and 2% dextrose, pH 4.5.).

2) 10× Protease Inhibitor Cocktail B: SCAT153

Evacuated 5 ml total volume plastic tubes containing (0.5 ml):10 µM biotinylated EPI-KAL2, 400 µg/mL polybrene, 20 mM EDTA, and 263 µM leupeptin, dissolved in acid-citrate-dextrose (100 mM trisodium citrate, 67 mM citric acid, and 2% dextrose, pH 4.5.).

Biotinylated EPI-KAL2 was included in the Protease Inhibitor Cocktail B (SCAT153). SCAT169 (Specialized Coagulation Assay Tubes, formulation 169) and SCAT153 (Specialized Coagulation Assay Tubes, formulation 153) tubes were stored at 2-8° C.

Example 2: SCAT169 and SCAT153 Tubes Prevent Contact System Activation as Shown by 2-Chain Western Blot Assay Plasma collected in either the SCAT169 or the SCAT153 tubes blocked contact system activation induced by ex vivo addition of ellagic acid (FIG. 1), a well-known contact system activator, as measured by the conversion of 1-chain to 2-chain HMWK by Western blot analysis.

Observed ellagic acid-induced contact system activation was compared between plasma samples collected in 3 different blood collection tubes: sodium citrate tubes (standard tubes used in clinical chemistry labs for coagulation measurements), SCAT169 tubes, and SCAT153 tubes.

1-chain HWMK was essentially completely consumed in sampled activated with ellagic acid in sodium citrate tubes, and the appearance of 2-chain HMWK was detected.

In contrast, 1-chain HMWK was preserved in ellagic acid-activated plasma from SCAT169 and SCAT153 tubes.

These results provided evidence that the SCAT169 and SCAT153 tubes are effective in preventing ex vivo contact system activation that can occur during plasma sample collection and processing.

Example 3: SCAT169 and SCAT153 Protease Inhibitor Cocktails Increased Plasma Clotting Times Plasma clotting times were measured in samples treated in 3 different blood collection tubes: sodium citrate tubes, SCAT169 tubes, and SCAT153 tubes, for three individual donor samples (Table 1).

As shown through prothrombin and activated partial thromboplastin, clotting time increased in samples with SCAT159 and SCAT153 as compared to sodium citrate. The results are provided in Table 3 below.

TABLE 3

Effect of the Protease Inhibitors on Plasma Clotting Times

| | Prothrombin Time (s) | | | Activated Partial Thromboplastin Time (s) | | |
|---|---|---|---|---|---|---|
| DONOR#: | Citrate | SCAT169 | SCAT 153 | Citrate | SCAT169 | SCAT 153 |
| 1 | 12.4 | 214.55 | 55.3 | 42.8 | >240 | >240 |
| 2 | 12.8 | 159.6 | 27.85 | 37.6 | >240 | >240 |
| 3 | 11.4 | >300 | 87.1 | 34.6 | >240 | >240 |

Example 4: Use of Evacuated Blood Collection Tubes for Assessing Endogenous Levels of Contact System Activation in Human Subjects Examination of plasma biomarkers of contact system activation is challenging due to inadvertent activation during blood collection and processing. In this study, the utility of specialized blood collection tubes (SCAT159 and SCAT153) in assessing levels of cleaved high-molecular-weight kininogen (cHMWK) in plasma from healthy subjects and those with Types I/II hereditary angioedema (HAE), idiopathic angioedema or HAE with normal C1-INH (HAEnC1, also referred to as nC1-INH) was investigated as follows.

To avoid artificial activation of the contact pathway during blood sampling, the study used standardized blood collection techniques and custom tubes containing protease inhibitors. Blood samples were collected from healthy subjects and the disease subjects noted above (during periods of disease quiescence and flare) to assess the percentage of cHMWK using a Western blot assay. The blood samples were placed in SCAT159 or SCAT153 tubes (5 mL total volume, 0.5 mL 10× protease inhibitor cocktail) using a catheter with a butterfly-type needle system. The blood samples were then processed to produce plasma samples within 1 hour after blood collection.

The SCAT tube plasma samples were analyzed by Simple Western (SBHD) and Western blot (TGA) to determine the level of cleaved kininogen (2-chain kininogen) in the plasma samples following methods disclosed in, e.g., WO 2015/061183.

Figure 2:
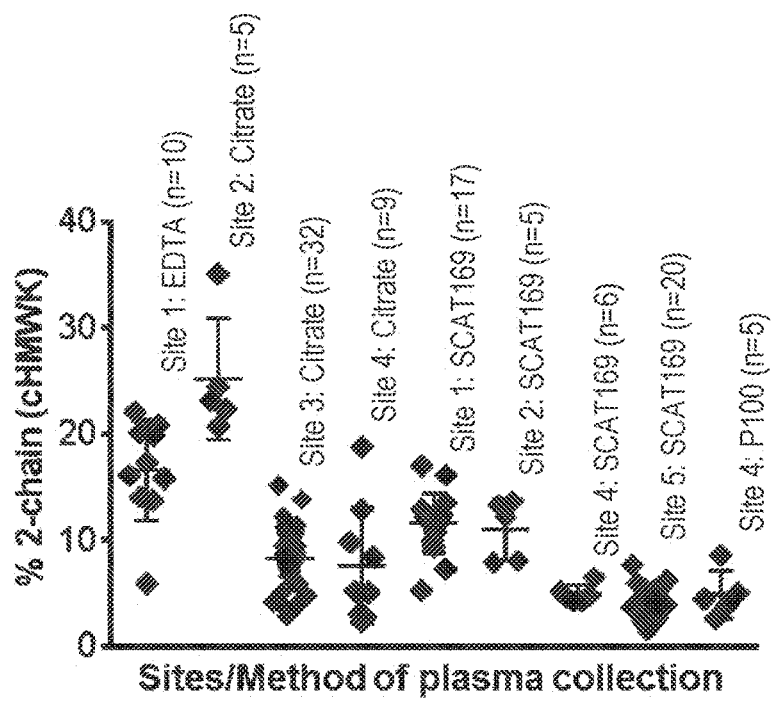
FIG. 2 is a graph showing variation of kininogen cleavage (percent 2-HMWK/cHMWK) based on sample collection methods in plasma from healthy subjects. The clinical site of collection, as well as the types of tubes used for collection, is indicated, including $K_2EDTA$ (EDTA), sodium citrate, SCAT169, or P100. The groupings of data points correspond to, from left to right, site 1: EDTA, site 2: citrate; site 3: citrate, site 4: citrate, site 1: SCAT169, site 2: SCAT169, site 4: SCAT169, site 5: SCAT169, and site 4: P100.

Plasma was collected from the healthy subjects at clinical sites 1-5 into plastic collection tubes containing various anti-coagulants, protease inhibitors, or protein stabilizers before being processed to plasma. Specifically, the types of tubes were $K_2$EDTA, sodium citrate, SCAT169 or P100 (BD Biosciences). As shown in FIG. 2, the tubes that were found to minimize ex vivo contact system activation contained protease inhibitors and were either P100 tubes or SCAT169 tubes, which were 5 mL volume plastic evacuated blood collection tubes containing 0.5 mL 10× concentrated mixture of 100 mM benzamidine, 400 µg/mL polybrene, 2 mg/mL soybean trypsin inhibitor, 20 mM EDTA, 263 µM leupeptin, and 20 mM AEBSF dissolved in acid-citrate-dextrose (100 mM trisodium citrate, 67 mM citric acid, and 2% dextrose, pH 4.5). Collection methods using tubes containing the protease inhibitor cocktails prevented elevation of cHMWK when healthy volunteer plasma was assayed.

Figure 3:
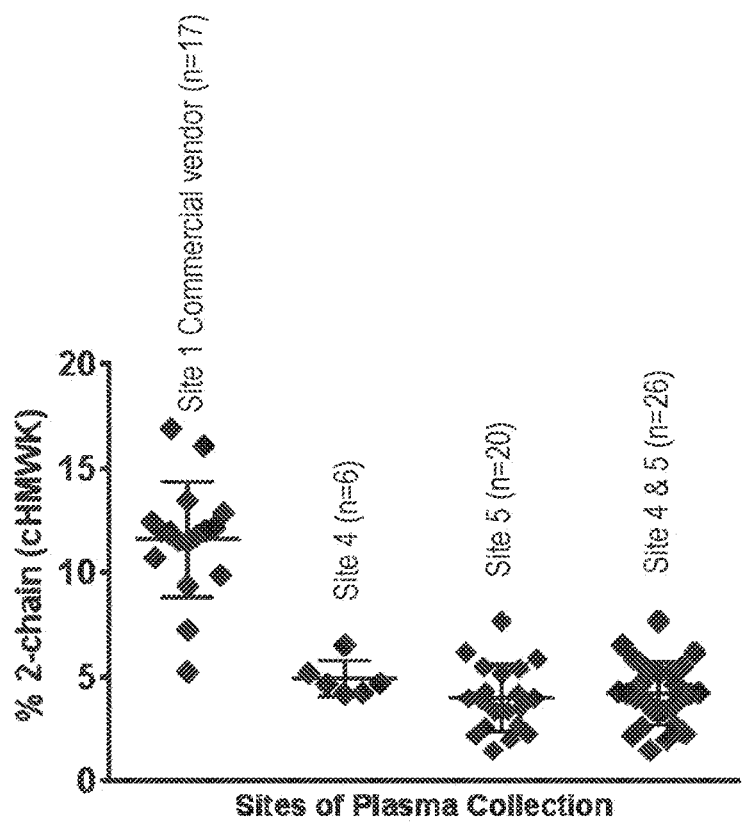
FIG. 3 is a graph showing kininogen cleavage (percent 2-HMWK/cHMWK) in plasma collected in SCAT 169 tubes from healthy subjects from different clinical sites. The groupings of data points correspond to, from left to right, site 1: commercial vendor, site 4, site 5, and sites 4 and 5.

Results obtained from this study showed that, in healthy subjects, levels of cHMWK were stable (<5%) at room temperature (RT) for at least 24 hours following blood collection into custom tubes, but the levels of cHMWK were elevated (12%) in plasma samples obtained from a commercial vendor, demonstrating the importance of optimizing blood collection techniques when examining contact pathway activation. protease The effects of kininogen cleavage in plasma collected into SCAT169 tubes from healthy subjects from two two different clinical sites (sites 4 and 5) and from a commercial vendor (site 1) was also evaluated (FIG. 3). The commercial vendor collected blood samples directly into the SCAT 169 tubes without an initial discard tube.

Figure 4:
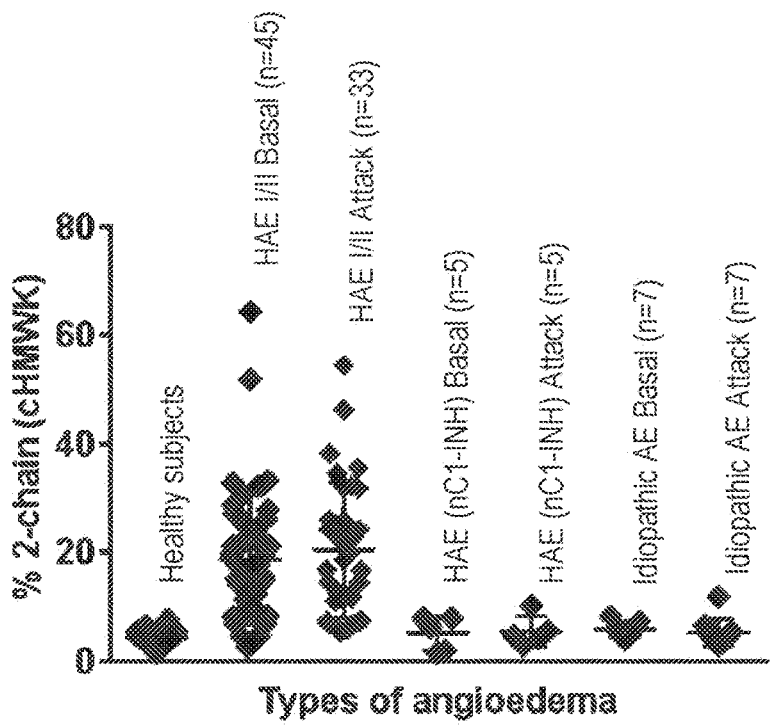
FIG. 4 is a graph showing kinongen cleavage (percent 2-HMWK/cHMWK) in healthy subjects as compared to subjects having type I or II HAE, nC1-INH HAE, and idiopathic angioedema (AE). The groupings of data points correspond to, from left to right, healthy subjects, HAE I/II basal, HAE I/II attack, HAE (nC1-INH) basal, HAE (nC1-INH) attack, idiopathic AE basal, and idiopathic AE attack.

Kininogen cleavage was also evaluated in blood samples collected in SCAT169 tubes from subjects having types of angioedema (type I/II HAE, nC1-INH HAE, and idiopathic AE). Plasma was collected from healthy subjects or subjects having various types of angioedema in both the quiescent state (basal) and during an attack (attack) to measure the amount of cHMWK in various disease states. cHMWK percentages were clearly elevated at baseline in subjects with HAE (n=21) compared to healthy controls (n=26) but not in plasma from subjects with idiopathic angioedema (n=4) or HAEnC1 (n=5) (FIG. 4), suggesting limited plasma kallikrein activity, although not excluding a role of contact pathway activation during acute attacks in those disorders.

Plasma evaluated for detection of cHMWK is vulnerable to contact system activation stimulated by the collection methods and tubes. In sum, this study provides a refined method for collection of plasma samples for evaluation of contact system activation, which prevents cleavage of HMWK ex vivo.

Example 5: Use of Evacuated Blood Collection Tubes for Assessing Endogenous Levels of Contact System Activation in Human Subjects The specialized blood collection tubes (SCAT159 and SCAT153) were evaluated for utility in assessing levels of cleaved high-molecular-weight kininogen (cHMWK) in plasma from healthy subjects and those with Types I/II hereditary angioedema (HAE).

Briefly, blood samples were collected from the healthy subjects and from patients having HAE, during periods of disease quiescence (basal) and flare (attack). The percentage of 2-chain HMWK in the plasma was detected using a Western blot assay. Plasma samples were collected from a phase 1b multicenter, double-blind study of randomized patients with HAE type I/II who received 2 subcutaneous doses of anti-pKal antibody (DX-2930) on days 0 and 15 in close groups of 30, 100, 300, or 400 mg or placebo. Blood samples were obtained prior to and after the anti-pKal antibody (DX-2930) on days 1, 8, 22, 64, 92, and 120.

Figure 5:
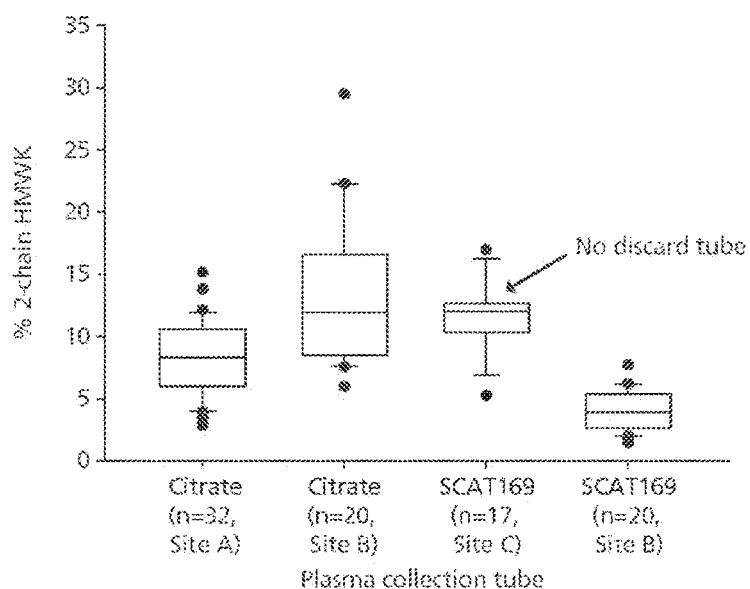
FIG. 5 is a graph showing 2-chain HMWK levels in plasma from healthy subjects and patients with HAE. A: shows the percentage of plasma 2-chain HMWK levels from healthy subjects. As indicated in the graph, clinical site C did not use an initial discard tube before collection of SCAT169 plasma. B: shows the percentage of plasma 2-chain HMWK levels from patients with HAE.
Figure 5:
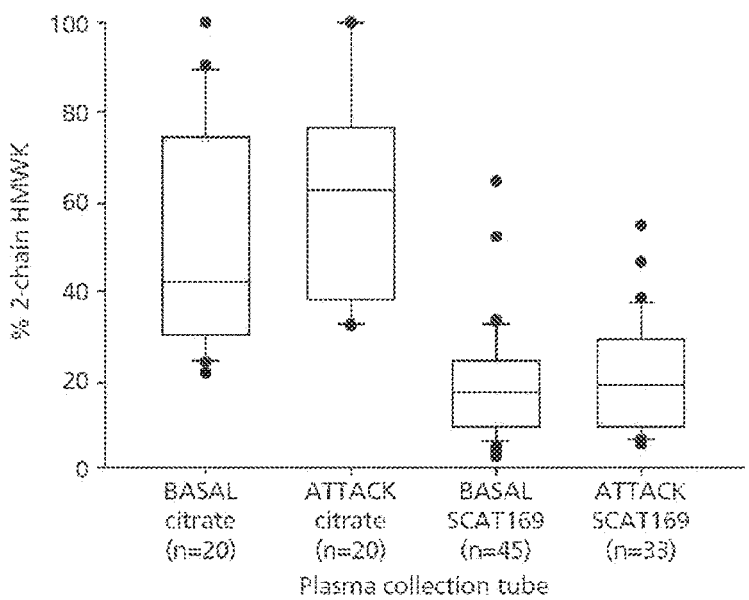

As shown in FIG. 5A, the percentage of plasma 2-chain HMWK levels in samples from healthy subjects collected from three different clinical sites (A, B, and C) varied with the collection method and type of tube used. Samples using sodium citrate tubes had higher levels of 2-chain HMWK, relative to samples in SCAT169 tubes. Notably, samples collected at clinical site C, which were collected directly into the SCAT169 tubes and did not use a discard tube prior to the tube containing the protease inhibitor cocktail, had higher levels of 2-chain HMWK as compared to samples using a discard tube.

Similarly, as shown in FIG. 5B, the percentage of plasma 2-chain HMWK levels in samples from HAE were higher in the sodium citrate tubes as compared to plasma collected in SCAT169 tubes, likely due to exogenous activation of the contact system associated with plasma collection and processing.

This study demonstrates the advantages of using the blood collection tubes containing the protease inhibitor cocktails, as described herein, and provides a refined method for collection of plasma samples for evaluation of contact system activation, which prevents aberrant contact system activation (e.g., shown by the cleavage of HMWK) ex vivo.

Example 6: Use of Evacuated Blood Collection Tubes for Assessing Plasma Drug Levels Blood is drawn from HAE patients treated with DX-2930 and healthy controls by routine practice and placed into collection tubes. After placing the initial blood samples in one or multiple collection tubes, 5 ml of the following blood sample is placed into SCAT159 or SCAT153 tubes. The blood samples are then processed to produce plasma samples within 1 hour after blood collection.

The amount of DX-2930 in the SCAT plasma samples are measured by standard immunoassays, for example, ELISA. Briefly, a Fab version of an anti-idiotypic monoclonal antibody against DX-2930 is coated onto the surface of a 96-well plate overnight and unbound anti-idiotypic Fab molecules are removed by washing the plate multiple times. The SCAT plasma samples are then added to the plate, which is incubated at room temperature for 2-3 hours. The plate is washed several times and a biotinylated IgG version of an anti-idiotypic monoclonal antibody against DX-2930 is added to the plate followed by an incubation step and a wash step. Horseradish peroxidase conjugated streptavidin is then added to the plate. After a 30' incubation, the plate is washed again and examined for a signal released by the dye. The intensity of the signal corresponds to the amount of DX-2930 in the plasma sample.

Example 7: Use of Evacuated Blood Collection Tubes for Assessing Drug Immunogenicity Plasma samples from HAE patients treated with DX-2930 are prepared from blood samples collected in SCAT159 or SCAT153 tubes, as disclosed above. Anti-DX-2930 antibodies in the plasma sample are isolated by solid phase extraction and acid dissociation (SPEAD).

Briefly, the plasma samples are incubated with biotinylated DX-2930 and incubated overnight. The mixture is then placed into a plate coated with streptavidin to capture biotinylated DX-2930, which bind to anti-DX-2930 antibodies in the plasma sample, if any. The anti-DX-2930 antibodies are then released by acid treatment and coated directly on a Meso Scale Discovery (MSD) plate. Ruthenium-labeled DX-2930 is added to the MSD plate and an electrochemiluminescent signal is measured to detect the presence of anti-DX-2930 antibodies.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS AND SCOPE

Those skilled in the art will recognize, or be able to ascertain using no more than routine experimentation, many equivalents to the specific embodiments of the present disclosure described herein. The scope of the present disclosure is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The present disclosure includes embodiments in which exactly one member of the group is present in, employed in, or otherwise relevant to a given product or process. The present disclosure includes embodiments in which more than one, or all of the group members are present in, employed in, or otherwise relevant to a given product or process.

Furthermore, the present disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the present disclosure, or aspects of the present disclosure, is/are referred to as comprising particular elements and/or features, certain embodiments of the present disclosure or aspects of the present disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the present disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the present disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. A method for assessing the endogenous level of contact system activation in a subject, the method comprising:
   (i) collecting blood from a subject to an evacuated blood collection tube;
   (ii) processing the blood to produce a plasma sample; and
   (iii) measuring the level of contact system activation in the plasma sample,
   wherein the evacuated blood collection tube comprises a liquid formulation that comprises a mixture of protease inhibitors, polybrene, and EDTA, wherein the mixture of protease inhibitors comprises benzamidine, soybean trypsin inhibitor, leupeptin, and 4-(2-aminoethyl) benzenesulfonyl fluoride hydrochloride (AEBSF).

2. A method for assessing the level of a drug targeting the contact system in a subject, the method comprising:
   (i) collecting blood from a subject to an evacuated blood collection tube; wherein the subject has been administered a drug that targets a component of the contact system;
   (ii) processing the blood to produce a plasma sample; and
   (iii) measuring the level of the drug in the plasma sample,
   wherein the evacuated blood collection tube comprises a liquid formulation that comprises a mixture of protease inhibitors, polybrene, and EDTA, wherein the mixture of protease inhibitors comprises benzamidine, soybean trypsin inhibitor, leupeptin, and 4-(2-aminoethyl) benzenesulfonyl fluoride hydrochloride (AEBSF).

3. A method for assessing immunogenicity of a drug targeting the contact system, the method comprising:
   (i) collecting blood from a subject to an evacuated blood collection tube; wherein the subject has been administered a drug that targets a component of the contact system;
   (ii) processing the blood to produce a plasma sample; and
   (iii) measuring the level of antibodies that bind to the drug in the plasma sample,
   wherein the evacuated blood collection tube comprises a liquid formulation that comprises a mixture of protease inhibitors, polybrene, and EDTA, wherein the mixture of protease inhibitors comprises benzamidine, soybean trypsin inhibitor, leupeptin, and 4-(2-aminoethyl) benzenesulfonyl fluoride hydrochloride (AEBSF).

4. The method of claim 1, wherein the tube is a non-glass tube.

5. The method of claim 1, wherein the liquid formulation comprises 80-120 mM benzamidine, 1-3 mg/ml soybean trypsin inhibitor, 200-300 μM leupeptin, and 10-30 mM AEBSF.

6. The method of claim 1, wherein the liquid formulation comprises 100 mM benzamidine, 2 mg/ml soybean trypsin inhibitor, 263 μM leupeptin, and 20 mM AEBSF.

7. The method of claim 1, wherein the polybrene is at a concentration of 400 μg/mL and the EDTA is at a concentration of 20 mM.

8. The method of claim 1, wherein the liquid formulation further comprises trisodium citrate, citric acid, and dextrose.

9. The method of claim 8, the trisodium citrate is at a concentration of 100 mM, the citric acid is at a concentration of 67 mM, and the dextrose is 2%.

10. The method of claim 1, wherein the liquid formulation has a pH of 4-6.

11. The method of claim 10, wherein the liquid formulation has a pH of 4.5.

12. The method of claim 1, wherein the mixture of protease inhibitors consists of benzamidine, soybean trypsin inhibitor, leupeptin, and AEBSF.

13. The method of claim 1, wherein in step (i), the evacuated blood collection tube is not the first tube filled with the blood from the subject; and/or step (ii) is performed within one hour after step (i).

14. The method of claim 1, wherein the subject is a human subject having a disease associated with the contact system.

15. The method of claim 14, wherein the disease is hereditary angioedema (HAE) or idiopathic angioedema.

16. The method of claim 14, wherein the human subject is treated with a drug targeting a component of the contact system, optionally plasma kallikrein (pKal).

17. The method of claim 16, wherein the drug inhibits active plasma kallikrein.

18. The method of claim 1, wherein step (iii) is performed by measuring the level of one or more biomarkers indicative of contact system activation.

19. The method of claim 18, wherein the one or more biomarkers are selected from the group consisting of prekallikrein, active plasma kallikrein (pKal), α2M-pKal complex, active Factor XII, active Factor XI, high molecular weight kininogen (HMWK), and a bradykinin metabolite.

20. The method of claim 3, wherein the method further comprises, prior to step (iii), isolating antibodies that bind to the drug from the plasma sample.

* * * * *

UNITED STATES PATENT AND TRADEMARK OFFICE
CERTIFICATE OF CORRECTION

| | | |
|---|---|---|
| PATENT NO. | : 10,870,115 B2 | Page 1 of 1 |
| APPLICATION NO. | : 15/752228 | |
| DATED | : December 22, 2020 | |
| INVENTOR(S) | : Sexton et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 212 days.

Signed and Sealed this
Thirty-first Day of January, 2023

Katherine Kelly Vidal
*Director of the United States Patent and Trademark Office*

SEQUENCE LISTING

```
<160> NUMBER OF SEQ ID NOS: 1

<210> SEQ ID NO 1
<211> LENGTH: 58
<212> TYPE: PRT
<213> ORGANISM: Artificial Sequence
<220> FEATURE:
<223> OTHER INFORMATION: Synthetic Polypeptide

<400> SEQUENCE: 1

Met His Ser Phe Cys Ala Phe Lys Ala Asp Asp Gly Pro Cys Arg Ala
1               5                   10                  15

Ala His Pro Arg Trp Phe Phe Asn Ile Phe Thr Arg Gln Cys Glu Glu
```

-continued

```
                    20                  25                  30
Phe Ser Tyr Gly Gly Cys Gly Gly Asn Gln Asn Arg Phe Glu Ser Leu
            35                  40                  45
Glu Glu Cys Lys Lys Met Cys Thr Arg Asp
    50                  55
```